(12) United States Patent
Nielsen et al.

(10) Patent No.: US 8,406,840 B2
(45) Date of Patent: Mar. 26, 2013

(54) SPATIALLY RESOLVED OXYMETRY

(75) Inventors: Tim Nielsen, Hamburg (DE); Thomas Koehler, Norderstedt (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 1413 days.

(21) Appl. No.: 12/066,561

(22) PCT Filed: Sep. 7, 2006

(86) PCT No.: PCT/IB2006/053144
§ 371 (c)(1),
(2), (4) Date: Mar. 12, 2008

(87) PCT Pub. No.: WO2007/031911
PCT Pub. Date: Mar. 22, 2007

(65) Prior Publication Data
US 2008/0242960 A1    Oct. 2, 2008

(30) Foreign Application Priority Data

Sep. 13, 2005  (EP) .................................... 05108411

(51) Int. Cl.
*A61B 5/00*     (2006.01)
(52) U.S. Cl. ........................................ 600/323; 600/310
(58) Field of Classification Search .................. 600/323, 600/425
See application file for complete search history.

(56) References Cited

U.S. PATENT DOCUMENTS

| 5,494,032 A | 2/1996 | Robinson et al. |
| 6,615,064 B1 * | 9/2003 | Aldrich .......................... 600/316 |
| 6,819,950 B2 * | 11/2004 | Mills ............................. 600/322 |
| 2002/0173723 A1 | 11/2002 | Lewis et al. |
| 2003/0212316 A1 | 11/2003 | Leiden et al. |
| 2004/0039268 A1 | 2/2004 | Barbour et al. |
| 2004/0147039 A1 | 7/2004 | Van Der Mark et al. |

FOREIGN PATENT DOCUMENTS

| DE | 3019234 A1 | 12/1981 |
| GB | 2402472 A | 12/2004 |

OTHER PUBLICATIONS

Jobsis. Machine translation of DE3019234 submitted by applicant. Mar. 23, 1981.*

* cited by examiner

*Primary Examiner* — Max Hindenburg
*Assistant Examiner* — Renee Danega

(57) ABSTRACT

In optical tomography, a calibration of the data may be necessary for image reconstruction. According to an exemplary embodiment of the present invention, the object of interest is used for calibration, wherein the image data is acquired during a highly oxygenated phase of the object of interest and wherein the calibration data is acquired during a low oxygenated phase of the object of interest. This may provide for an improved calibration, resulting in improved image quality.

18 Claims, 2 Drawing Sheets

SPATIALLY RESOLVED OXYMETRY

The invention relates to the field of optical imaging. In particular, the invention relates to an optical examination apparatus for optical examination of an object of interest, to a method of examining an object of interest with an optical examination apparatus, an image processing device, a computer-readable medium and a program element.

Optical tomography is one of the most promising methods for early detection of breast tumours. The method is based on the changing of optical properties of the affected tissue. For most types of tumours two effects are typical: First, the blood concentration in tumour tissue grows and second, the blood oxygenation decreases. Therefore, some tumours show increased vascularization and hypoxia, i.e. low oxygenation. Thus, blood volume or equivalently total haemoglobin (Hb) concentration and oxygenation of tissue are potential tumour markers.

Both quantities can be determined from absorption measurements at multiple near-infrared wavelengths because the absorption spectra of oxy-Hb and deoxy-Hb are different. For spatially resolved measurements of oxygenation and Hb concentration a tomographic data acquisition and subsequent image reconstruction may be necessary. However, a difficulty in tomographic measurements with NIR-light is that scattering dominates the light propagation in tissue. A thorough calibration of the data may be necessary for successful image reconstruction.

Typical problems that have to be solved by the data calibration are: the transmission of the optics, changes in coupling the light into the tissue, changes of the position of the source and detector fibers. Many of the calibration factors which are related to the measurement equipment can be determined by a reference measurement on a known reference object. This reference object should by as similar as possible to the measurement object as possible.

It may be desirable to have an improved calibration of acquired data.

According to an exemplary embodiment of the present invention, an optical examination apparatus for optical examination of an object of interest may be provided, the optical examination apparatus comprising a detector unit adapted for detecting first radiation and second radiation from the object of interest, resulting in first detection data and second detection data. Furthermore, a determination unit may be provided adapted for determining spatially resolved information relating to the object of interest on the basis of the first detection data and the second detection data, wherein the first detection data corresponds to a first oxygen concentration inside the object of interest and wherein the second detection data corresponds to a second oxygen concentration inside the object of interest, which is different from the first oxygen concentration.

Therefore, according to this exemplary embodiment of the present invention, a calibration of detection data may be provided, which uses detection data acquired from the same object. The first radiation may be called image radiation and the second radiation may be called calibration radiation. In other words, no separate calibration medium is used for calibration of the data. Therefore, the calibration may be improved, since the optical properties of the object of interest and the reference medium (which is the same as the object of interest) are equal over the entire range of wavelengths.

It should be noted, that the first detection data may not only relate to a single measurement but may relate to a plurality of measurements, e.g. at different illumination conditions. Accordingly, the second detection data may not only relate to another single measurement but may relate to a plurality of measurements, e.g. at different illumination conditions.

According to another exemplary embodiment of the present invention, the optical examination apparatus further comprises an optical radiation source adapted for emitting primary optical radiation to the object of interest.

Thus, a primary radiation beam may be emitted to the object of interest. The primary radiation beam may, for example, have a near-infrared wavelength and may be directed to a certain region inside the object of interest. Furthermore, the primary radiation beam may comprise intensity-modulated laser light of different wavelength. However, no modulation of the primary radiation beam and no use of different wavelengths is necessary for carrying out the invention.

According to another exemplary embodiment of the present invention, the determination unit is adapted for reconstructing a two-dimensional or three-dimensional image of the object of interest on the basis of the first detection data and the second detection data.

According to another exemplary embodiment of the present invention, the first detection data corresponds to a systolic phase of the object of interest and the second detection data corresponds to a diastolic phase of the object of interest.

Therefore, the first detection data or image data may be acquired at a high oxygen (systolic) concentration inside the object of interest and the second image data or calibration data may be acquired during a low oxygen (diastolic) concentration inside the object of interest.

According to another exemplary embodiment of the present invention, the optical examination apparatus further comprises an electrocardiogram unit adapted for acquiring electrocardiogram data of the object of interest during the detection of the first radiation and the second radiation by the detector unit, wherein the determination unit is adapted for identifying the systolic phase and therefore the first detection data and for identifying the diastolic phase and therefore the second detection data on the basis of the electrocardiogram data.

For example, the object of interest may be a breast of a female patient and the ECG data may be acquired by monitoring the heart-beat of the patient. This may provide for an automated optical examination which performs a calibration of the acquired data on the basis of the heart cycle.

According to another exemplary embodiment of the present invention, the determination unit is adapted for reconstructing blood dynamics of the object of interest on the basis of a temporal behaviour of the first radiation and the second radiation.

For example, not only one single image is calculated but a sequence of images, resulting in a movie reflecting dynamic changes inside the object of interest. Thus, the first data may be acquired during a phase of low oxygen concentration in the blood (e.g., when the patient is breathing gas with reduced oxygen concentration). Multiple second data sets are the acquired at multiple different time intervals, each corresponding to a different oxygen concentration in the blood and in the tissue (e.g., because the patient has started to breathe gas with a high oxygen concentration). The multiple time intervals during which the second data sets are acquired correspond to a sequence of measurements from which a film is constructed. The film may show, how the perfusion develops during time. In other words, the ratio between the first data and that second data set which is acquired at the first time interval shows only changes in the blood vessels and the ratios between the first data and the following second data sets which are acquired at later times show the perfusion of the tissue.

Thus, according to this exemplary embodiment of the present invention, both, the transmission and the reflection is measured.

According to another exemplary embodiment of the present invention, the optical examination apparatus is adapted as an optical mammography apparatus.

Therefore, a safe, painless, and cost-effective technique may be provided for the detection and diagnosis of breast cancer.

Since photons at optical wavelengths are not harmful to biological tissue, as are for instance X-ray photons, the system according to the invention is appropriate for medical applications, since the optical imaging modalities according to the invention do not destroy tissue of a human being.

Next, exemplary embodiments of the optical examination apparatus will be described. However, these embodiments also apply for the optical examination method, the image processing device, the computer-readable medium and the program element.

The optical radiation detector unit may be a spatially resolving detector. By combining the calibration procedure with the spatial resolution of a detector (for instance a charge coupled device (CCD) array), the accuracy of the resulting image may be improved.

Additionally or alternatively, the detector unit may be a frequency or energy resolving detector.

Additionally or alternatively, the optical detector unit may be a time resolving detector.

According to another exemplary embodiment of the present invention, the information relating to the object of interest is determined on the basis of a ratio of the first detection data and the second detection data.

This may provide for an effective and fast calibration procedure.

According to another exemplary embodiment of the present invention, a method of examining an object of interest with an optical examination apparatus may be provided, the method comprising the steps of detecting first radiation and second radiation from the object of interest, resulting in first detection data and second detection data, and determining information relating to the object of interest on the basis of the first detection data and the second detection data. The first detection data corresponds to a first oxygen concentration inside the object of interest and the second detection data corresponds to a second, different oxygen concentration inside the object of interest.

It is believed that this may allow for an improved calibration of the detection data, which may result in an improved image quality.

According to another exemplary embodiment of the present invention, the method further comprising the step of acquiring electrocardiogram data of the object of interest during the detection of the first radiation and the second radiation, identifying the systolic phase and therefore the first detection data, and identifying the diastolic phase and therefore the second detection data on the basis of the electrocardiogram data.

According to another exemplary embodiment of the present invention, an image processing device for examining an object of interest with an optical examination apparatus may be provided, the image processing device comprising a memory for storing first detection data and second detection data and a determination unit adapted for determining information relating to the object of interest on the basis of the first detection data and the second detection data.

According to another exemplary embodiment of the present invention, a computer-readable medium may be provided, in which a computer program of examining an object of interest with an optical examination apparatus is stored which, when being executed by a processor, is adapted to carry out the above-mentioned method steps.

The present invention also relates to a program element of examining an object of interest, which, when being executed by a processor, is adapted to carry out the above-mentioned method steps. The program element may be stored on a computer-readable medium and may be loaded into working memories of a data processor. The data processor may thus be equipped to carry out exemplary embodiments of the methods of the present invention. The computer program may be written in any suitable programming language, for example, C++ and may be stored on the computer-readable medium, such as a CD-ROM. Also, the computer program may be available from a network, such as the WorldWideWeb, from which it may be downloaded into image processing units or processors, or any suitable computers.

It may be seen as the gist of an exemplary embodiment of the present invention, that, in optical tomography, a calibration of the data is provided without using an extra calibration medium. According to an exemplary embodiment of the present invention, the object of interest is used for calibration, wherein the image data is acquired during a highly oxygenated phase of the object of interest and wherein the calibration data is acquired during a low oxygenated phase of the object of interest. This may provide for an improved calibration and result in an improved image quality.

These and other aspects of the present invention will become apparent from and elucidated with reference to the embodiments described hereinafter.

Exemplary embodiments of the present invention will be described in the following, with reference to the following drawings.

The illustration in the drawings is schematically. In different drawings, similar or identical elements are provided with the same reference numerals.

Figure 1:
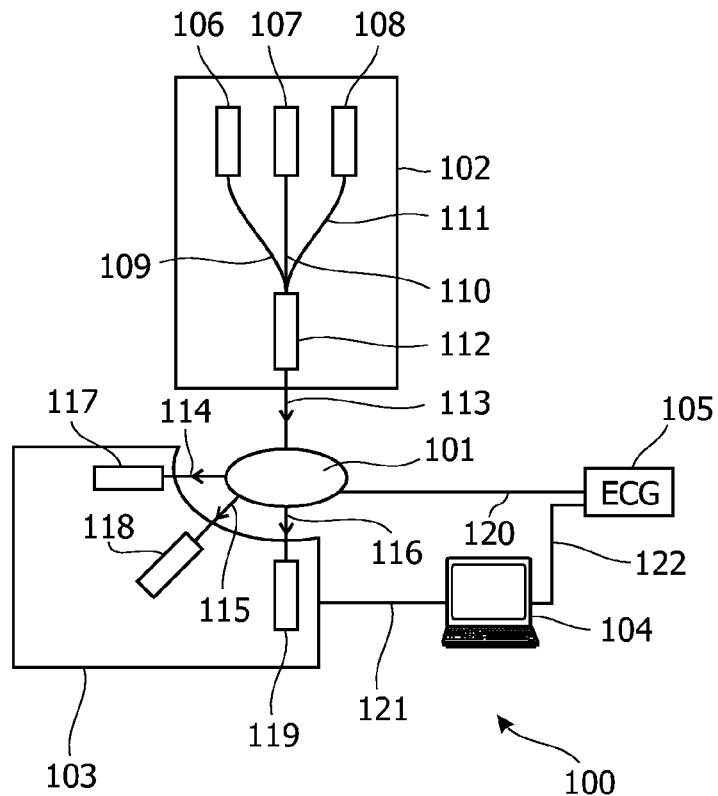
FIG. 1 shows a simplified schematic representation of an optical examination apparatus according to an exemplary embodiment of the present invention.

In the following, referring to FIG. 1, an optical examination apparatus 100 according to an exemplary embodiment of the invention will be described in detail.

The optical examination apparatus 100 for examination of an object of interest 101, such as, for example, tissue, comprises an optical radiation source 102, a detection unit 103, a determination unit 104 and as an option an electrocardiogram unit 105.

The optical radiation source 102 may comprise one or a plurality of lasers or photodiodes 106, 107, 108, each being adapted for emitting a particular wavelength. Each emitted wavelength may be an infrared or near-infrared wavelength, for example between 500 nm and 1500 nm. The emitted light beams may be delivered to a coupler 112 by optical fibres 109, 110, 111. The fibre coupler 112 may be adapted for coupling the three fibres 109, 110, 111 and for emitting the combined light 113 to the object of interest 101 by direct illumination of the imaging field.

However, the examination apparatus may use more fibers as sources, e.g. 255 fibers, and e.g. 255 fibers for detection. According to an exemplary embodiment of the present invention, the fibers are mounted in the wall of a cup shaped measurement chamber. The source fibers are illuminated sequentially using continuous waves, and the signal of all detectors is recorded simultaneously. E.g. three different wavelengths may be used.

It should be noted, that instead of optical fibres or additionally to optical fibres 109, 110, 111, other optical elements, such as lenses (not depicted in FIG. 1) may be used for delivering the light to the object of interest 101. Furthermore, filters, mirrors, apertures and modulators may be used for pre-processing the light. However, one single wavelength may be necessary according to an exemplary embodiment of the present invention.

The light emitted by the optical radiation source 102 impinges on the sample 101 and propagates through it. Due to the diffuse nature of the light propagation the object of interest 101 emits transmitted radiation 114, 115, 116.

The light which is emitted from the object of interest 101 may be further processed by light collection optics (not depicted in FIG. 1), which may comprise optical elements such as lenses, mirrors, and filters.

The light may be filtered in an emission filter (not depicted in FIG. 1). Any background radiation can be rejected from the collection pathway by one or a series of optical filters.

Then, the light from the object of interest 101 is detected by detector elements 117, 118, 119, which may be adapted in form of a CCD camera, photo diode, avalanche photodiode or a multiplier tube. An amplification of the detection signal may be performed and the detected signal may be converted into a digital signal.

The detected signal, which comprises first detection data corresponding to a first oxygen concentration inside the object of interest and second detection data corresponding to a second oxygen concentration inside the object of interest (which is different from the first oxygen concentration) is then transmitted to a determination unit 104 by transmission line 121.

The determination unit 104 may be coupled (via line 122) to an electrocardiogram unit 105 adapted for measuring the heart cycle of the object of interest 101 via line 120. This electrocardiogram data may then be used for identifying diastolic phases and systolic phases of the heart of the object of interest resulting in an identification of first detection data and second detection data.

The determination unit 104 is adapted for reconstructing a two-dimensional or a three-dimensional image of the object of interest 101 on the basis of the (high oxygen) image data and the (low oxygen) calibration data.

The reconstruction algorithm is for example based on a Rytov-approximation, which is a linear approximation to the diffusion equation based on first-order perturbation theory. The baseline for the perturbation is defined by the first measurement which results in the first detection data ($\Phi_0(x_d, x_s)$). Using the Rytov-approximation, the change of the absorption coefficient $\delta\mu$ between the second detection data ($\Phi(x_d, x_s)$) and the first detection data ($\Phi_0(x_d, x_s)$) can be written as $$\ln\frac{\Phi(x_d, x_s)}{\Phi_0(x_d, x_s)} = c \int \delta\mu(x) \frac{G(x, x_d)G(x, x_s)}{G(x_d, x_s)} dx,$$

where $x_s$ and $x_d$ refer to the positions of the sources and the detectors, respectively. $G(x, x_s)$ is the Green's function at point x for a point source at $x_s$. c is a constant depending on the optical properties of the object of interest at the first oxygen concentration. Now, the above equation has to be solved for $\delta\mu$, which then results in the image of the object of interest.

However, a thorough calibration of the data is necessary for successful image reconstruction. Therefore, a reference measurement is used to calibrate the data. From the ratio of the measurement data and the reference data, the difference in attenuation between the reference medium and the breast can be reconstructed. According to an aspect of the present invention, the reference medium is the object of interest itself (i.e. the breast for example), only at a different oxygen concentration of the blood inside the breast. Therefore, there is no mismatch between the optical properties of the reference medium and the optical properties of the object of interest (because they are the same).

In other words, two sets of measurements data from the object of interest are acquired, one corresponding to the systolic phase of the heart and the other corresponding to the diastolic phase of the heart. The ratio of both data sets depends only on the difference of the attenuation related to blood oxygenation and Hb concentration between the systolic and diastolic phase. In this way not only systematic factors of the measurement system like fibre transmission, detector sensitivity, etc. cancel but also the mismatch between reference medium and object of interest as well as any static inhomogeneities of the tissue. This may simplify the image reconstruction of blood parameters considerably.

Alternatively, the data can be stored time-resolved with a parallel ECG recording. The modulation of the signal may then be used to determine the systolic and diastolic phase retrospectively. Furthermore, the entire temporal behaviour may be used to reconstruct the blood dynamics.

By increasing the number of radiation sources, changes in the blood volume and changes in the oxygen saturation may be discriminated.

It should be noted that, according to the invention, it is not necessary to use a plurality of different wavelengths. One single wavelength may be sufficient. Furthermore, according to an aspect of the present invention, no spectral resolution is necessary for detection. Furthermore, it should be noted that the first and second data may not correspond to systolic and diastolic phases of the heart, but to a phase of normal breathing and to a second phase during which the patient holds its breath (in order to decrease the oxygen concentration in the blood).

A data acquisition (measuring the refection/transmission) may be performed at different areas around the object of interest during which acquisition no change in the illumination condition is performed. Then, subsequent data acquisitions may be performed at the (same or other) different areas around the object of interest but with changed illumination conditions. All these data acquisitions result in the first detection data. The same data acquisition sequence is then performed at a different oxygen concentration, resulting in the second detection data.

The oxygenation may also be affected by other means like breathing gas with different oxygen concentration.

Furthermore, oxygenation and blood volume may also be changed by drugs or physiological processes (e.g., exercise (muscles), stimulation/activity (brain)).

However, in any of these cases the first dataset would correspond to one state of oxygenation and blood volume and the second dataset would correspond to the other state of oxygenation and blood volume.

A dynamic process can be studied by acquiring a series of second datasets during the dynamic process while the first dataset would be acquired in a stationary state of the object.

Figure 2:
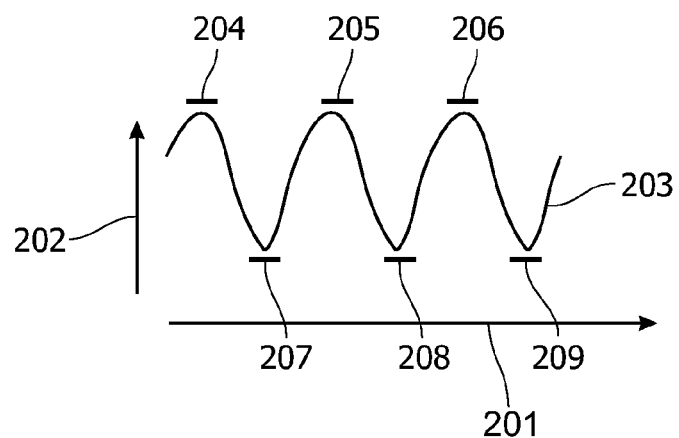
FIG. 2 shows a schematic representation of an absorption curve during multiple heart beats comprising systolic and diastolic phases of the object of interest.

FIG. 2 shows absorption data comprising systolic and diastolic phases of the object of interest. Horizontal axis 201 represents the time and vertical axis 202 represents the absorption of the tissue represented by curve 203. The corresponding electrocardiogram data is represented by intervals 204, 205, 206, which correspond to systolic phases of the object of interest and intervals 207, 208, 209, which correspond to diastolic phases of the object of interest. Curve 203 represents a measured data set, comprising data measured over multiple heart cycles.

As may be seen from FIG. 2, the absorption changes between systolic phases and diastolic phases.

Figure 3:
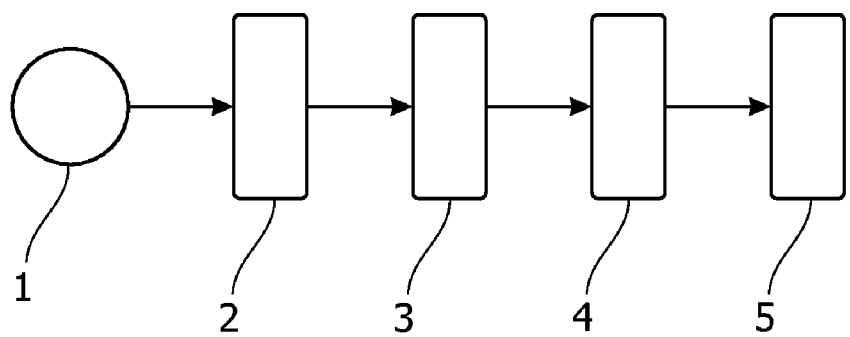
FIG. 3 shows a flow-chart of an exemplary embodiment of a method according to the present invention.

FIG. 3 shows a flow-chart of an exemplary embodiment according to the present invention. The method starts at step 1 with the emission of primary optical radiation to the object of interest by an optical radiation source.

Then, in step 2, a data acquisition is performed. A detector unit detects image radiation and calibration radiation from the object of interest, resulting in first detection data and second detection data.

Then, in step 3, a ratio between the first detection data and the second detection data is determined for calibration.

In step 4, a reconstruction of the image of the object of interest is performed on the basis of the ratio.

The method ends in step 5.

Figure 4:
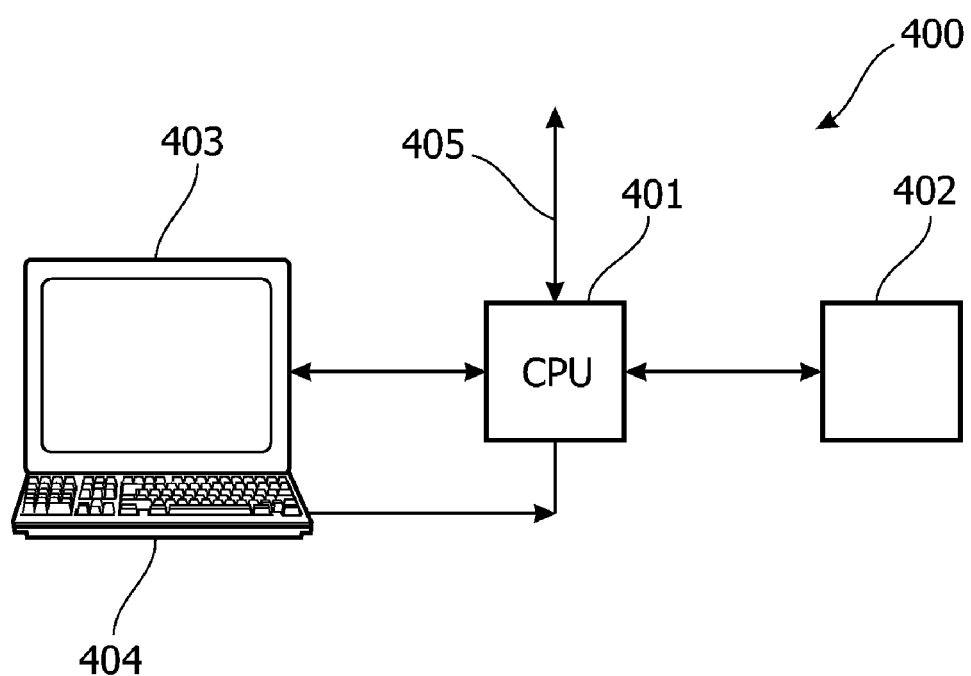
FIG. 4 shows an exemplary embodiment of an image processing device according to the present invention for executing an exemplary embodiment of a method in accordance with the present invention.

FIG. 4 depicts an exemplary embodiment of an image processing device according to the present invention for executing an exemplary embodiment of the method in accordance with the present invention. The image processing device 400 depicted in FIG. 4 comprises a central processing unit (CPU) or image processor 401 connected to a memory 402 for storing an image depicting an object of interest, such as a breast or other piece of tissue. The data processor 401 may be connected to a plurality of input/output network for diagnosis devices, such as an optical tomography device. The data processor 401 may furthermore be connected to a display device 403, for example, a computer monitor, for displaying information or an image computed or adapted in the data processor 401. An operator or user may interact with the data processor 401 via a keyboard 404 and/or other output devices, which are not depicted in FIG. 4.

Furthermore, via the bus system 405, it may also be possible to connect the image processing and control processor 401 to, for example, a motion monitor, which monitors a motion of the object of interest. For example, the motion sensor may be an exhalation sensor or an electrocardiogram unit.

Exemplary embodiments of the invention may be sold as a software option to imaging work stations.

It should be noted that the term "comprising" does not exclude other elements or steps and the "a" or "an" does not exclude a plurality and that a single processor or system may fulfill the functions of several means or units recited in the claims. Also elements described in association with different embodiments may be combined.

It should also be noted, that any reference signs in the claims shall not be construed as limiting the scope of claims.

The invention claimed is:

1. An optical examination apparatus for optical examination of an object of interest, the optical examination apparatus comprising:
    a detector unit adapted for detecting first radiation and second radiation from the object of interest in response to light emitted from an optical radiation source propagating through the object of interest, the first radiation and the second radiation providing first detection data and second detection data, respectively; and
    a determination unit adapted for determining spatially resolved information relating to the object of interest based on the first detection data and the second detection data,
    wherein the first detection data corresponds to a first oxygen concentration inside the object of interest,
    wherein the second detection data corresponds to a second oxygen concentration inside the object of interest, which is different from the first oxygen concentration, and
    wherein the spatially resolved information relating to the object of interest is determined using a ratio of the first detection data and the second detection data for calibration.

2. The optical examination apparatus of claim 1, wherein the optical radiation source comprises a coupler adapted for coupling light emitted by a plurality of lasers or photodiodes, and emitting the coupled light to the object of interest.

3. The optical examination apparatus of claim 1, wherein the determination unit is adapted for reconstructing a two-dimensional or three-dimensional image of the object of interest based on the first detection data and the second detection data.

4. The optical examination apparatus of claim 1, wherein the first detection data corresponds to a systolic phase of the object of interest; and wherein the second detection data corresponds to a diastolic phase of the object of interest.

5. The optical examination apparatus of claim 4, further comprising:
    an electrocardiogram unit adapted for acquiring electrocardiogram data of the object of interest during the detection of the first radiation and the second radiation by the detector unit;
    wherein the determination unit is adapted for identifying the systolic phase and therefore the first detection data and for identifying the diastolic phase and therefore the second detection data based on electrocardiogram data.

6. The optical examination apparatus of claim 1, wherein the determination unit is adapted for reconstructing blood dynamics of the object of interest on the basis of a temporal behaviour of the first radiation and the second radiation.

7. The optical examination apparatus of claim 1, wherein the detector unit is adapted for detecting, as the first detection data, first and second transmission data and, as the second detection data, first and second reflection data.

8. The optical examination apparatus of claim 1, adapted as an optical mammography apparatus.

9. The optical examination apparatus of claim 1, wherein the detector unit comprises a spatially resolving detector.

10. The optical examination apparatus of claim 1, wherein the detector unit comprises a frequency resolving detector or an energy resolving detector.

11. The optical examination apparatus of claim 1, wherein the detector unit comprises a time resolving detector.

12. The optical examination apparatus of claim 1, wherein the first radiation and the second radiation have the same wavelength.

13. The optical examination apparatus of claim 1, wherein the determination unit determines the spatially resolved information relating to the object of interest using the second detection data for calibration.

14. A method of examining an object of interest with an optical examination apparatus, the method comprising:
   detecting light from the object of interest, responsive to optical radiation from an optical radiation source propagating through the object of interest, the detected light comprising first detection data and second detection data; and
   determining spatially resolved information relating to the object of interest based on the first detection data and the second detection data,
   wherein the first detection data corresponds to a first oxygen concentration inside the object of interest while the primary optical radiation propagates through the object of interest,
   wherein the second detection data corresponds to a second oxygen concentration inside the object of interest, which is different from the first oxygen concentration, while the primary optical radiation propagates through the object of interest, and
   wherein determining the spatially resolved information relating to the object of interest comprises:
      determining a ratio between the first detection data and the second detection data for calibration; and
      reconstructing an image of the object of interest based on the ratio.

15. An image processing device for examining an object of interest with an optical examination apparatus, the image processing device comprising:
   a memory for storing first detection data and second detection data obtained from light propagating through the object of interest emitted by an optical radiation source; and
   a determination unit adapted for determining spatially resolved information relating to the object of interest based on the first detection data and the second detection data;
   wherein the first detection data corresponds to a first oxygen concentration inside the object of interest; and
   wherein the second detection data corresponds to a second oxygen concentration inside the object of interest, which is different from the first oxygen concentration.

16. A computer-readable medium, in which a computer program for examining an object of interest with an optical examination apparatus is stored which, when being executed by a processor, is adapted to carry out the steps of:
   detecting light from the object of interest, responsive to optical radiation emitted by an optical radiation source and propagating through the object of interest, the detected light comprising first detection data and second detection data; and
   determining spatially resolved information relating to the object of interest based on the first detection data and the second detection data;
   wherein the first detection data corresponds to a first oxygen concentration inside the object of interest while the optical radiation propagates through the object of interest; and
   wherein the second detection data corresponds to a second oxygen concentration inside the object of interest, which is different from the first oxygen concentration, while the optical radiation propagates through the object of interest.

17. A program element of examining an object of interest, which, when being executed by a processor, is adapted to carry out the steps of:
   detecting light from the object of interest, responsive to optical radiation emitted by an optical radiation source and propagating through the object of interest, the detected light comprising first detection data and second detection data; and
   determining spatially resolved information relating to the object of interest based on the first detection data and the second detection data;
   wherein the first detection data corresponds to a first oxygen concentration inside the object of interest while the optical radiation propagates through the object of interest; and
   wherein the second detection data corresponds to a second oxygen concentration inside the object of interest, which is different from the first oxygen concentration, while the optical radiation propagates through the object of interest.

18. The method of claim 14, further comprising:
   acquiring electrocardiogram data of the object of interest during the detection of the light from the object of interest;
   identifying a systolic phase based on the electrocardiogram data, the first detection data being detected during the systolic phase; and
   identifying a diastolic phase based on the electrocardiogram data, the second detection data being detected during the diastolic phase.

* * * * *